United States Patent [19]
Dubief et al.

[11] Patent Number: 6,090,376
[45] Date of Patent: *Jul. 18, 2000

[54] TOPICAL COMPOSITION COMPRISING A POLYMER WITH SILICONE GRAFTS AND AN AMPHIPHILIC POLYMER WITH A FATTY CHAIN

[75] Inventors: Claude Dubief, Chesnay; Christine Dupuis, Paris, both of France

[73] Assignee: L'Oreal, Paris, France

[*] Notice: This patent issued on a continued prosecution application filed under 37 CFR 1.53(d), and is subject to the twenty year patent term provisions of 35 U.S.C. 154(a)(2).

[21] Appl. No.: 08/720,439

[22] Filed: Mar. 19, 1999

[30] Foreign Application Priority Data

Sep. 29, 1995 [FR] France ................................. 95-11483

[51] Int. Cl.$^7$ .............. A61K 7/06; A61K 7/11; A61K 7/075
[52] U.S. Cl. ................... 424/70.12; 424/DIG. 1; 424/DIG. 2
[58] Field of Search ................ 424/401, 70.12, 424/70.16, DIG. 1, DIG. 2; 510/122; 525/69, 424

[56] References Cited

U.S. PATENT DOCUMENTS

| | | |
|---|---|---|
| 4,693,935 | 9/1987 | Mazurek . |
| 4,728,571 | 3/1988 | Clemens et al. . |
| 4,972,037 | 11/1990 | Garbe et al. . |
| 5,362,485 | 11/1994 | Hayama et al. . |
| 5,622,694 | 4/1997 | Torgerson et al. . |

FOREIGN PATENT DOCUMENTS

| | | |
|---|---|---|
| 412704 | 2/1991 | European Pat. Off. . |
| 412706 | 2/1991 | European Pat. Off. . |
| 412707 | 2/1991 | European Pat. Off. . |
| 524612 | 1/1993 | European Pat. Off. . |
| 582152 | 2/1994 | European Pat. Off. . |
| 2709955 | 3/1995 | France . |
| WO 91/15186 | 10/1991 | WIPO . |
| WO 95/00108 | 1/1995 | WIPO . |
| WO 95/00578 | 1/1995 | WIPO . |
| WO 95/04518 | 2/1995 | WIPO . |
| WO 95/05800 | 3/1995 | WIPO . |

Primary Examiner—Edward J. Webman
Attorney, Agent, or Firm—Finnegan, Henderson, Farabow, Garrett & Dunner, L.L.P.

[57] ABSTRACT

The present invention relates to a cosmetic or dermatological composition for the treatment of keratinous substances, in particular human hair, comprising, in a cosmetically or dermatologically acceptable medium, at least one grafted silicone polymer with a non-silicone organic skeleton grafted by monomers containing a polysiloxane and at least one ionic amphiphilic polymer containing at least one fatty chain and at least one hydrophilic unit.

The compositions according to the invention are in particular used as products which are rinsed out or as products which are not rinsed out, in particular for washing, caring for or conditioning the hair, form retention of the hair style or shaping of the hair style.

41 Claims, No Drawings

TOPICAL COMPOSITION COMPRISING A POLYMER WITH SILICONE GRAFTS AND AN AMPHIPHILIC POLYMER WITH A FATTY CHAIN

The present invention relates to a cosmetic or dermatological composition for the treatment of keratinous substances, particularly human hair, comprising at least one grafted silicone polymer with a non-silicone organic skeleton grafted by monomers containing a polysiloxane and at least one ionic amphiphilic polymer containing at least one fatty chain and at least one hydrophilic unit.

Polymers of the silicone polymer with a non-silicone organic skeleton grafted by monomers containing a polysiloxane type are known in the prior art for their styling properties. They are particularly advantageous in hair cosmetics owing to the fact that they contribute hold to hair. Their cosmetic properties after application to hair are nevertheless unsatisfactory. It is found that the hair exhibits, after application of these polymers, a rough and abrasive feel resulting from a non-continuous distribution of the polymer along the hair fibres.

The inventors have found that certain conventional thickening agents, such as, for example, crosslinked poly(acrylic acid) homopolymers, used in hair compositions containing these specific polymers had a tendency to decrease the viscosity of the composition and did not make it possible to substantially improve the distribution of the composition along wet or dry hair fibres or to substantially improve the properties of smoothness to the touch or of disentangling, after application.

The inventors have surprisingly discovered that the use of an ionic amphiphilic polymer containing at least one fatty chain and at least one hydrophilic unit as thickening agent in hair compositions containing a polymer with a non-silicone organic skeleton grafted by monomers containing a polysiloxane made it possible not only to increase the viscosity of the medium of these compositions but also to improve, on application, the deposition of the grafted silicone polymer along the keratinous fibres and to improve their cosmetic properties, in particular as regards feel and as regards disentangling, while retaining the styling properties of the grafted silicone polymer.

The composition according to the invention is therefore characterized in that it contains, in a cosmetically or dermatologically acceptable medium, at least one grafted silicone polymer with a non-silicone organic skeleton grafted by monomers containing a polysiloxane and at least one ionic amphiphilic polymer containing at least one fatty chain and at least one hydrophilic unit.

In the following, silicone or polysiloxane is understood to denote, in conformity with what is generally accepted, any organosilicon polymer or oligomer with a branched or crosslinked, linear or cyclic structure of variable molecular weight obtained by polymerization and/or polycondensation of suitably functionalized silanes and essentially composed of a repetition of main units in which the silicon atoms are connected to one another via oxygen atoms (siloxane bond ≡Si—O—Si≡), optionally substituted hydrocarbon radicals being directly bonded via a carbon atom to the said silicon atoms. The most common hydrocarbon radicals are alkyl radicals, particularly $C_1$–$C_{10}$ alkyl radicals and more particularly methyl radicals, fluoroalkyl radicals, aryl radicals and in particular phenyl radicals, and alkenyl radicals and particularly vinyl radicals; other types of radicals capable of being bonded either directly or via a hydrocarbon radical to the siloxane chain inlcude, but are not limited to, hydrogen, halogens, and in particular chlorine, bromine or fluorine, thiols, alkoxy radicals, polyoxyalkylene (or polyether) radicals and in particular polyoxyethylene and/or polyoxypropylene radicals, hydroxyl or hydroxyalkyl radicals, amino groups, which may or may not be substituted, amide groups, acyloxy or acyloxyalkyl radicals, hydroxyalkylamino or aminoalkyl radicals, quaternary ammonium groups, and amphoteric or betaine groups or anionic groups, such as carboxylates, thioglycolates, sulphosuccinates, thiosulphates, phosphates and sulphates (so-called "organomodified" silicones).

In the following, "polysiloxane macromer" is understood to denote, in conformity with what is generally accepted, any monomer containing, in its structure, a polymer chain of the polysiloxane type.

The silicone polymers in accordance with the present invention are preferably composed of an organic main chain formed from organic monomers not containing silicone, on which is grafted, within the said main chain and optionally at at least one of its ends, at least one polysiloxane macromer.

The non-silicone organic monomers constituting the main chain of the grafted silicone polymer can be chosen from monomers with ethylenic unsaturation polymerizable by the radical route, monomers polymerizable by polycondensation, such as those forming polyamides, polyesters or polyurethanes, or monomers with ring opening, such as those of the oxazoline or caprolactone type.

The grafted silicone polymers of the invention can be obtained according to any means known to a person skilled in the art, in particular by reaction between (i) a starting polysiloxane macromer correctly functionalized on the polysiloxane chain and (ii) one or more non-silicone organic compounds, themselves correctly functionalized by a functional group which is capable of reacting with the functional group or groups carried by the said silicone with the formation of a covalent bond; a classic example of such a reaction is the radical reaction between a vinyl group carried on one of the ends of the silicone and a double bond of a monomer with ethylenic unsaturation of the main chain.

The polymers with a non-silicone organic skeleton grafted by monomers containing a polysiloxane in accordance with the invention are more preferentially chosen from those described in U.S. Pat. Nos. 4,693,935, 4,728,571 and 4,972,037 and Patent Applications EP-A-0,412,704, EP-A-0,412,707, EP-A-0,640,105 and WO 95/00578, all of which are incorporated herein by reference. They relate to copolymers obtained by radical polymerization from monomers with ethylenic unsaturation and from silicone macromers having an end vinyl group or alternatively to copolymers obtained by reaction of a polyolefin comprising functionalized groups and of a polysiloxane macromer having an end functional group which is reactive with the said functionalized groups.

A specific family of silicone polymers that is suitable for the implementation of the present invention is composed of the grafted silicone copolymers comprising:

a) from 0 to 98 weight % of at least one lipophilic monomer (A) of low lipophilic polarity with ethylenic unsaturation which is polymerizable by the radical route;

b) from 0 to 98 weight % of at least one polar hydrophilic monomer (B) with ethylenic unsaturation which is copolymerizable with the monomer or monomers of the type (A);

c) from 0.01 to 50 weight % of at least one polysiloxane macromer (C) of general formula:

$$X(Y)_n Si(R)_{3-m} Z_m \qquad (I)$$

where:

X denotes a vinyl group which is copolymerizable with the monomers (A) and (B);

Y denotes a group with divalent bonding;

R denotes a hydrogen, a $C_1$–$C_6$ alkyl or alkoxy or a $C_6$–$C_{12}$ aryl;

Z denotes a monovalent polysiloxane unit having a number-average molecular weight of at least 500;

n is 0 or 1 and m is an integer ranging from 1 to 3, the percentages being calculated with respect to the total weight of the monomers (A), (B) and (C).

These polymers, and processes for the preparation thereof, are described in U.S. Pat. Nos. 4,693,935, 4,728,571 and 4,972,037 and Patent Applications EP-A-0,412,704, EP-A-0,412,707 and EP-A-0,640,105. They have a number-average molecular weight preferably ranging from 10,000 to 2,000,000 and a glass transition temperature Tg or a crystalline melting temperature Tm preferably of at least –20° C.

Mention may be made, as examples of lipophilic monomers (A), of esters of acrylic or methacrylic acid with $C_1$–$C_{18}$ alcohols; styrene; polystyrene macromers; vinyl acetate; vinyl propionate; α-methylstyrene; tert-butylstyrene; butadiene; cyclohexadiene; ethylene; propylene; vinyltoluene; esters of acrylic or methacrylic acid with 1,1-dihydro-perfluoroalkanol or with its homologues; esters of acrylic or methacrylic acid with ω-hydrofluoroalkanol; esters of acrylic or methacrylic acid with fluoroalkyl-sulphoamidoalcohol; esters of acrylic or methacrylic acid with fluoroalkyl alcohol; esters of acrylic or methacrylic acid with alcohol fluoroether; or their mixtures.

The preferential monomers (A) are chosen from the group composed of n-butyl methacrylate, isobutyl methacrylate, tert-butyl acrylate, tert-butyl methacrylate, 2-ethylhexyl methacrylate, methyl methacrylate, 2-(N-butylperfluorooctanesulphonamido)-ethyl acrylate, 2-(N-methylperfluorooctane-sulphonamido)ethyl acrylate and their mixtures.

Mention may be made, as examples of polar monomers (B), acrylic acid, methacrylic acid, N,N-dimethylacrylamide, dimethylaminoethyl methacrylate, quaternized dimethylaminoethyl methacrylate, (meth) acrylamide, N-t-butylacrylamide, maleic acid, maleic anhydride and its half esters, hydroxyalkyl (meth)acrylates, diallyldimethylammonium chloride, vinylpyrrolidone, vinyl ethers, maleimides, vinylpyridine, vinylimidazole, polar heterocyclic vinyl compounds, styrenesulphonate, allyl alcohol, vinyl alcohol, vinylcaprolactam or their mixtures. The preferential monomers (B) are chosen from the group composed of crylic acid, N,N-dimethyl-acrylamide, dimethylaminoethyl methacrylate, quaternized dimethylaminoethyl methacrylate, vinylpyrrolidone and their mixtures.

The preferred polysiloxane macromers (C) of formula (I) are chosen from those corresponding to the following formula (II):

$$CHR^1 = CR^2 - \overset{O}{\underset{\|}{C}} - O - (CH_2)_{\overline{q}} - (O)_P - Si(R^3)_{3-m} - (-O - \underset{\underset{CH_3}{|}}{\overset{\overset{CH_3}{|}}{Si}} -)_{\overline{r}} - R^4 \quad (II)$$

in which:

$R^1$ is hydrogen or —COOH;

$R^2$ is hydrogen, methyl or —CH$_2$COOH;

$R^3$ is $C_1$–$C_6$ alkyl, alkoxy or alkylamino, $C_6$–$C_{12}$ aryl or hydroxyl;

$R^4$ is $C_1$–$C_6$ alkyl, alkoxy or alkylamino, $C_{6-C12}$ aryl or hydroxyl;

q is an integer from 2 to 6;

p is 0 or 1;

r is an integer from 5 to 700;

m is an integer ranging from 1 to 3 (preferably 1).

Use is more particularly made of the polysiocane macromes of formula:

$$CH_2=C-\overset{O}{\underset{\|}{C}}-O-(CH_2)_3-\underset{\underset{CH_3}{|}}{\overset{\overset{CH_3}{|}}{Si}}-O\left[\underset{\underset{CH_3}{|}}{\overset{\overset{CH_3}{|}}{Si}}-O\right]_n\underset{\underset{CH_3}{|}}{\overset{\overset{CH_3}{|}}{Si}}-(CH_2)_3-CH_3$$
$$\underset{CH_3}{|}$$

with n being a number ranging from 5 to 700.

A specific embodiment of the invention comprises the use of a copolymer capable of being obtained by radical polymerization from the mixture of monomers consisting of:

a) 60 weight % of term-butyl acrylate;

b) 20 weight % of acrylic acid;

c) 20 weight % of silicone macromer of formula:

$$CH_2=C-\overset{O}{\underset{\|}{C}}-O-(CH_2)_3-\underset{\underset{CH_3}{|}}{\overset{\overset{CH_3}{|}}{Si}}-O\left[\underset{\underset{CH_3}{|}}{\overset{\overset{CH_3}{|}}{Si}}-O\right]_n\underset{\underset{CH_3}{|}}{\overset{\overset{CH_3}{|}}{Si}}-(CH_2)_3-CH_3$$
$$\underset{CH_3}{|}$$

with n being a number ranging from 5 to 700, the percentages by weight being calculated with respect to the total weight of the monomers.

Another specific embodiment of the invention comprises the use of a copolymer capable of being obtained by radical polymerization from the mixture of monomers consisting of:

a) 80 weight % of tert-butyl acrylate;

b) 20 weight % of silicone macromer of formula:

$$CH_2=C-\overset{O}{\underset{\|}{C}}-O-(CH_2)_3-\underset{\underset{CH_3}{|}}{\overset{\overset{CH_3}{|}}{Si}}-O\left[\underset{\underset{CH_3}{|}}{\overset{\overset{CH_3}{|}}{Si}}-O\right]_n\underset{\underset{CH_3}{|}}{\overset{\overset{CH_3}{|}}{Si}}-(CH_2)_3-CH_3$$
$$\underset{CH_3}{|}$$

with n being a number ranging from 5 to 700, the percentages by weight being calculated with respect to the total weight of the monomers.

Another specific family of silicone polymers suitable for the implementation of the present invention is composed of the grafted silicone copolymers capable of being obtained by reactive extrusion of a polysiloxane macromer having an end reactive functional group with a polymer of the polyolefin type containing reactive groups capable of reacting with the end reactive functional group of the polysiloxane macromer in order to form a covalent bond enabling the silicone to be grafted to the main chain of the polyolefin.

These polymers, and the process for the preparation thereof, are described in Patent Application WO 95/00578.

The reactive polyolefines are preferably chosen from the group composed of polyethylenes or polymers of monomers derived from ethylene, such as propylene, styrene, alkylstyrene, butylene, butadiene, (meth)acrylate, vinyl esters or equivalents, containing reactive functional groups capable of reacting with the end functional group of the polysiloxane macromer. They are more preferably chosen from the group composed of copolymers of ethylene or of ethylene derivatives and of monomers chosen from those containing a carboxyl functional group, such as (meth) acrylic acid; those containing an acid anhydride functional group, such as the anhydride of maleic acid; those containing an acid chloride functional group, such as chloride of(meth)acrylic acid; those containing an ester functional group, such as the esters of (meth)acrylic acid; or those containing an isocyanate functional group.

The silicone macromers are preferably chosen from polysiloxanes containing a functionalized group at the end of the polysiloxane chain or close to the end of the chain, chosen from the group composed of alcohols, thiols, epoxy groups or primary and secondary amines and more particularly from those corresponding to the general formula (III):

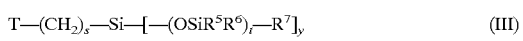

$$T-(CH_2)_s-Si-[-(OSiR^5R^6)_t-R^7]_y \quad (III)$$

in which T is chosen from the group composed of $NH_2$, NHR', an epoxy functional group, OH or SH; $R^5$, $R^6$, $R^7$ and R' independently denote a $C_1$–$C_6$ alkyl, phenyl, benzyl or $C_6$–$C_{12}$ alkylphenyl or hydrogen; s is a number from 2 to 100; t is a number from 0 to 1000 and y is a number from 1 to 3. They have a number-average molecular weight preferably ranging from 5000 to 300,000, more preferably from 8000 to 200,000, and most preferably from 9000 to 40,000.

The grafted silicone polymers of the invention are preferably used in an amount ranging from 0.01 to 20 weight % of the total weight of the composition. More preferably this amount varies from 0.1 to 15 weight % and still more preferably from 0.5 to 10 weight %.

The ionic amphiphilic polymers containing at least one fatty chain and hydrophilic units used according to the invention are preferably chosen from the group composed of:

(1) ionic holosides modified by groups containing at least one fatty chain; mention may be made, by way of example, of:

quaternized cationic celluloses modified by groups containing at least one fatty chain, such as alkyl, arylalkyl or alkylaryl groups or their mixtures where the alkyl groups are preferably $C_8$–$C_{22}$ groups;

(cationic) quaternized alkylhydroxyethylcelluloses, such as the products QUATRISOFt LM 200, QUATRISOFT LM-X 529-18-A, QUATRISOFT LM-X 529-18-B ($C_{12}$ alkyl) and QUATRISOFT LM-X 529-8 ($C_{18}$ alkyl) sold by the company Amerchol and the products CRODACEL QM, CRODACEL QL ($C_{12}$ alkyl) and CRODACEL QS ($C_{18}$ alkyl) sold by the company Croda;

anionic saccharide ($C_{12}$–$C_{18}$) polyalcohols, such as the product EMULSAN (D-galactosamine/aminouronic acid mixture) sold by the company Petroferm;

(2) copolymers of maleic anhydride and of monomers containing at least one fatty chain; mention may be made, by way of example, of:

n-octadecyl vinyl ether/maleic anhydride copolymers, such as the product GANTREZ AN-8194 sold by the company ISP;

(3) copolymers of crotonic acid and of monomers containing at least one fatty chain; mention may be made, by way of example, of:

vinyl acetate/crotonic acid/allyl stearate terpolymers;

(4) copolymers of (meth)acrylic acid and of monomers containing at least one fatty chain; these monomers are chosen from hydrophobic monomers with a fatty chain, amphiphilic monomers containing a hydrophobic part with a fatty chain and a hydrophilic part, or alternatively their mixtures; mention may be made, by way of example, of:

crosslinked copolymers of acrylic acid/$C_{10}$–$C_{30}$ alkyl acrylate, such as the products PEMULEN TR 1, PEMULEN TR 2, CARBOPOL 1382, CARBOPOL 1342 and CARBOPOL ETD 2020 sold by the company Goodrich;

(meth)acrylic acid/ethyl acrylate/alkyl acrylate copolymers, such as the product ACUSOL 823 sold by the company Rohm & Haas and the product Imperon R sold by the company Hoechst;

crosslinked acrylic acid/vinyl isodecanoate copolymers, such as the product STABYLEN 30 sold by the company 3V;

acrylic acid/vinylpyrrolidone/lauryl methacrylate terpolymers, such as the products ACRYLIDONE LM, ACP-1184 and ACP-1194 sold by the company ISP;

acrylic acid/lauryl (meth)acrylate copolymers, such as the products COATEX SX sold by the company Coatex;

(meth)acrylic acid/alkyl acrylate/polyethoxylated alkyl allyl ether terpolymers, such as the products RHEOVIS-CR, -CR3, -CR2 and -CRX sold by the company Allied Colloids;

methacrylic acid/ethyl acrylate/polyethoxylated stearyl allyl ether terpolymers, such as the products SALCARE-SC90 and -SC80 sold by the company Allied Colloids (stearyl polyethoxylated with 10 mol of ethylene oxide, labelled steareth-10);

methacrylic acidlethyl acrylate/polyoxyethylenated lauryl acrylate terpolymers, such as the product RHEO 2000 sold by Coatex;

methacrylic acid/ethyl acrylate/polyoxyethylenated stearyl methacrylate terpolymers, such as the products ACRYSOL 22, ACRYSOL 25 and DW-1206A sold by the company Rohm & Haas;

methacrylic acid/ethyl acrylate/polyoxyethylenated nonylphenyl acrylate copolymers, such as the product RHEO 3000 sold by Coatex;

acrylic acid/polyoxyethylenated stearyl monoitaconate copolymers or acrylic acid/ polyoxyethylenated cetyl monoitaconate copolymers, such as the products 8069-72A and 8069-72B sold by National Starch;

methacrylic acid/butyl acrylate/hydrophobic monomer containing a fatty chain copolymers, such as the product 8069-146A sold by National Starch;

acrylic acid/$C_{15}$ alkyl acrylate/polyethylene glycol acrylate (28 mol of ethylene oxide) terpolymers, such as the product DAPRAL GE 202 sold by the company Akzo;

salts of a partial fatty acid ester of an acrylic acid/dimethylethanolamine copolymer, such as the product DAPRAL GE 202 DMA sold by the company Akzo;

acrylic acid/acrylate/amphiphilic monomer containing a fatty chain with urethane groups copolymers, such as the product ADDITOL VXW 1312 sold by Hoechst;

acrylic copolymers modified by hydrophobic groups with a fatty chain, such as the product ACUSOL 102 sold by Rohm & Haas.

The amphiphilic polymers containing at least one fatty chain and at least one hydrophilic unit according to the invention are preferably used in an amount of between 0.01 and 20 weight % of the total weight of the composition. More preferably, this amount varies from 0.1 to 15 weight % and still more more preferentially from 0.5 to 10 weight %.

The cosmetically or dermatologically acceptable medium is preferably composed of water or a mixture of water and of cosmetically acceptable solvents, such as monoalcohols, polyalcohols, glycol ethers or fatty acid esters, which can be used alone or as a mixture.

Mention may more particularly be made of lower alcohols, such as ethanol or isopropanol, polyalcohols, such as diethylene glycol, or glycol ethers, such as the alkyl ethers of glycol or of diethylene glycol.

The grafted silicone polymers according to the invention can be dissolved in the cosmetically acceptable medium or used in the form of an aqueous dispersion of particles.

The composition of the invention can also contain at least one additive chosen from thickeners without a fatty chain, fatty acid esters, esters of fatty acids and of glycerol, silicones, surfactants, fragrances, preservatives, sunscreening agents, proteins, vitamins, polymers, vegetable, animal, mineral or synthetic oils and any other additive conventionally used in the cosmetics field.

These additives are present in the composition according to the invention in proportions which can range from 0 to 20 weight % with respect to the total weight of the composition. The precise amount of each additive depends on its nature and is easily determined by the person skilled in the art.

Of course, the person skilled in the art will take care to choose the optional compound or compounds to be added to the composition according to the invention so that the advantageous properties intrinsically attached to the composition in accordance with the invention are not, or not substantially, detrimentally affected by the envisaged addition.

The compositions according to the invention can be provided in the gel, milk, cream, more or less thickened lotion or foam form.

They are more particularly hairsetting lotions, blow drying lotions, fixing compositions (lacquers) and styling compositions. The lotions can be packaged in various forms, in particular in vaporizers or pump-action sprays or in aerosol containers, in order to ensure application of the composition in the vaporized form or in the foam form. Such packaging forms are indicated, for example, when it is desired to obtain a spray, a lacquer or a foam for fixing or treating the hair.

The compositions can also be shampoos or compositions which are or are not to be rinsed out, to be applied before or after shampooing, dying, bleaching, permanent waving or hair straightening.

When the composition according to the invention is packaged in the form of an aerosol, for the purpose of obtaining a lacquer or an aerosol foam, it comprises at least one propellent agent which can be chosen from volatile hydrocarbons, such as n-butane, propane, isobutane, pentane, a chlorinated and/or fluorinated hydrocarbon and their mixtures. It is also possible to use, as propellent agent, carbon dioxide gas, nitrous oxide, dimethyl ether, nitrogen, compressed air and their mixtures.

A further subject of the invention is a non-therapeutic process for the treatment of keratinous substances, such as human hair, which comprises the application to the latter of a composition as defined above and then an optional rinsing with water.

The invention will now be more fully illustrated using the following examples which should not be regarded as limiting it to the embodiments described.

EXAMPLES

Example 1: Styling Gel

Grafted silicone polymer of structure (1) as defined below 0.5 g of AM

Methacrylic acid/ethyl acrylate/oxyethylenated stearyl methacrylate (55135110) terpolymer as a 30 % aqueous dispersion sold under the name Acrysol 22 by the company Rohm & Haas 1 g of AM Aminomethylpropanol, 100 % neutralization of the said silicone polymer and of the terpolymer q.s. for pH 7.5

Demineralized water q.s. for 100 g

Structure (1):

Copolymer obtained by radical polymerization from the mixture of monomers consisting of:
a) 60 weight % of tert-butyl acrylate;
b) 20 weight % of acrylic acid;
c) 20 weight % of silicone macromer of formula:

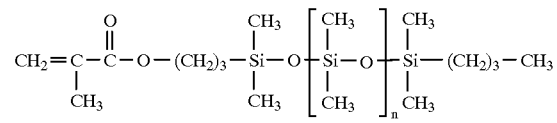

with n being a number chosen so that the number-average molecular weight of the macromer is between approximately 9000 and 12,000, the percentages by weight being calculated with respect to the total weight of the monomers.

COMPARATIVE VISCOSITY TESTS

The rheological properties of a conventional thickening agent of the crosslinked poly(acrylic acid) homopolymer type, such as the product SYNTHALEN K sold by the company 3V, were studied in an aqueous solution containing 1 weight % of this thickener and in an aqueous solution containing 1 weight % of this thickener and 1 weight % of grafted silicone polymer as described in Example 1. The viscosities of the thickened solutions were measured by means of a Rheomat 180 device equipped with the Contraves TV system. All the solutions were neutralized to pH 7.5 with aminomethylpropanol.

The rheological properties of an ionic amphiphilic polymer $P_1$ containing a fatty chain and at least one hydrophilic unit according to the invention were studied in an aqueous solution containing 1 weight % of this thickening amphiphilic polymer and in an aqueous solution containing 1 weight % of this thickener and 1 weight % of grafted silicone polymer as described in Example 1.

The amphiphilic polymer $P_1$ according to the invention which was studied is as follows:

$P_1$: Methacrylic acid/ethyl acrylate/oxyethylenated stearyl methacrylate (55/35/10) terpolymer as a 30% aqueous dispersion sold under the name ACRYSOL 22 by the company Rohm & Haas.

The viscosities of the solutions are shown in centipoises in the following table:

| Polymer studied | Viscosity in cps of the aqueous solution containing 1% of thickening agent alone or the grafted silicone polymer alone | Viscosity in cps of the aqueous solution containing 1 weight % of thickening agent and 1 weight % of grafted silicone polymer of Example 1 |
|---|---|---|
| Grafted silicone polymer of Example 1 | 40 | no thickening |
| Crosslinked poly(acrylic acid) homopolymer | 7500 | 3580 |
| $P_1$ | 1700 | 14,000 |

It is found that the crosslinked poly(acrylic acid) homopolymer, in combination with the grafted silicone polymer of the invention, decreases the viscosity of the formulation whereas the ionic amphiphilic thickening polymer $P_1$ according to the invention, containing a fatty chain and at least one hydrophilic unit, substantially increases the viscosity of the solution containing the grafted silicone polymer.

COMPARATIVE TESTS ON THE COSMETIC PROPERTIES

A sensory appraisal test was carried out with respect to a panel of 5 people. The disentangling and the smoothness to the touch, after application to wet and sensitized locks of hair of SA 20 type, were studied as cosmetic criteria. The three following solutions A, B and C were applied, with respect to each of these 5 people, on locks which had been shampooed beforehand, at a dose of 0.5 g per 5 g of lock:

Solution A containing 1 weight % of the grafted silicone polymer of Example 1;

Solution B containing 1 weight % of the grafted silicone polymer of Example 1 and 1 weight % of the crosslinked poly(acrylic acid) homopolymer Synthalen K;

Solution C (according to the invention) containing 1 weight % of the grafted silicone polymer of Example 1 and 1 weight % of polymer $P_1$ described above.

All the solutions A, B and C were neutralized to pH 7.5 with aminomethylpropanol.

For each cosmetic criterion, the people tested attribute an assessment grade from 0 to 5. The results of the tests are summarized in the table below.

| Solutions tested | Assessment of the disentangling | Assessment of the smoothness to the touch |
|---|---|---|
| A | 2 | 1.5 |
| B | 3 | 2.5 |
| C | 3.5 | 3 |

The 5 people questioned estimated that the presence of the thickening ionic amphiphilic polymer with a fatty chain and at least one hydrophilic unit according to the invention in the solution C containing the grafted silicone polymer improved the smoothness of the hair to the touch and the disentangling of the hair with respect to the solution A containing the grafted silicone polymer alone or the solution B containing the said grafted silicone polymer in combination with the conventional thickener of the crosslinked poly(acrylic acid) homopolymer type.

We claim:

1. A cosmetic or dermatological composition for the treatment of a keratinous substance, comprising, in a cosmetically or dermatologically acceptable medium,
    at least one grafted silicone polymer with a non-silicone organic skeleton grafted by at least one polysiloxane monomer, and
    at least one ionic amphiphilic polymer comprising at least one fatty chain and at least one hydrophilic unit, with the exception of crosslinked copolymers of acrylic acid and $C_{10}$–$C_{30}$ alkyl acrylates.

2. A cosmetic or dermatological composition for the treatment of a keratinous substance, comprising, in a cosmetically or dermatologically acceptable medium,
    at least one grafted silicone polymer comprising an organic skeleton formed from at least one non-silicone organic monomer and at least one polysiloxane monomer grafted thereon, and
    at least one ionic amphiphilic polymer comprising at least one fatty chain and at least one hydrophilic unit, with the exception of crosslinked copolymers of acrylic acid and $C_{10}$–$C_{30}$ alkyl acrylates.

3. A composition according to claim 2, wherein said at least one non-silicone organic monomer is selected from monomers with ethylenic unsaturation polymerizable by the radical route, monomers polymerizable by polycondensation and monomers with ring opening.

4. A composition according to claim 1, wherein said grafted silicone polymer comprises:
    a) from 0 to 98 weight % of at least one residue of a lipophilic monomer (A) of low polarity with ethylenic unsaturation of low polarity, wherein said at least one lipophilic monomer (A) is polymerizable by the radical route;
    b) from 0 to 98 weight % of at least one residue of a polar hydrophilic monomer (B) with ethylenic unsaturation, wherein said at least one polar hydrophilic monomer (B) is copolymerizable with said at least one lipophilic monomer (A); and
    c) from 0.01 to 50 weight % of at least one residue of a polysiloxane macromer (C) of general formula:

$$X(Y)_n Si(R)_{3-m} Z_m \qquad (I)$$

wherein:
    X is a vinyl group which is copolymerizable with said at least one lipophilic monomer (A) and said at least one polar hydrophilic monomer (B);
    Y is a group having divalent bonding;
    R is hydrogen, $C_1$–$C_6$ alkyl, $C_1$–$C_6$ alkoxy or $C_{6-C,2}$ aryl;
    Z is a monovalent polysiloxane unit having a number-average molecular weight of at least 500;
    n is 0 or 1; and
    m is an integer ranging from 1 to 3, the percentages being calculated with respect to the total weight of said monomers (A) and (B) and said macromer (C), and wherein at least one residue of monomer (A) or monomer (B) is present.

5. A composition according to claim 4, wherein said at least one lipophilic monomer (A) is selected from esters of acrylic or methacrylic acid with $C_1$–$C_{18}$ alcohols; styrene; polystyrene macromers; vinyl acetate; vinyl propionate; α-methylstyrene; tert-butylstyrene; butadiene; cyclohexadiene; ethylene; propylene; vinyltoluene; esters of acrylic or methacrylic acid with 1,1-dihydro-perfluoroalkanol or with its homologues; esters of acrylic or methacrylic acid with ω-hydrofluoroalkanol; esters of acrylic or methacrylic acid with fluoroalkyl-sulphoamidoalcohol; esters of acrylic or methacrylic acid with fluoroalkyl alcohol; and esters of acrylic or methacrylic acid with alcohol fluoroether.

6. A composition according to claim 4, wherein said at least one lipophilic monomer (A) is selected from n-butyl methacrylate, isobutyl methacrylate, tert-butyl acrylate, tert-butyl methacrylate, 2-ethylhexyl methacrylate, methyl methacrylate, 2-(N-butylperfluorooctanesulphonamido)-ethyl acrylate, and 2-(N-methylperfluorooctanesulphonamido)ethyl acrylate.

7. A composition according to claim 4, wherein said at least one polar hydrophilic monomer (B) is selected from acrylic acid, methacrylic acid, N,N-dimethylacrylamide, dimethylaminoethyl methacrylate, quaternized dimethylaminoethyl methacrylate, (meth)acrylamide, N-t- butylacrylamide, maleic acid, maleic anhydride and its half esters, hydroxyalkyl (meth)acrylates, diallyldimethylammonium chloride, vinylpyrrolidone, vinyl ethers, maleimides, vinylpyridine, vinylimidazole, polar heterocyclic vinyl compounds, styrenesulphonate, allyl alcohol, vinyl alcohol, and vinylcaprolactam.

8. A composition according to claim 7, wherein said at least one polar hydrophilic monomer (B) is selected from acrylic acid, N,N-dimethylacrylamide, dimethylaminoethyl methacrylate, quaternized dimethylaminoethyl methacrylate, and vinylpyrrolidone.

9. A composition according to claim 4, wherein said at least one polysiloxane macromer (C) corresponds to the following formula (II):

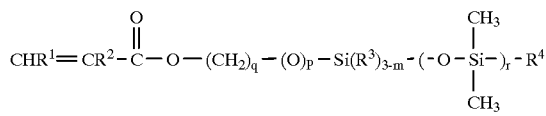

wherein:

$R^1$ is hydrogen or —COOH;

$R^2$ is hydrogen, methyl or —CH$_2$COOH;

$R^3$ is $C_1$–$C_6$ alkyl, $C_1$–$C_6$ alkoxy, $C_1$–$C_6$ alkylamino, $C_{6-C12}$ aryl or hydroxyl;

$R^4$ is $C_1$–$C_6$ alkyl, $C_1$–$C_6$ alkoxy, $C_1$–$C_6$ alkylamino, $C_{6-C12}$ aryl or hydroxyl;

q is an integer from 2 to 6;

p is 0 or 1;

r is an integer from 5 to 700; and m is an integer ranging from 1 to 3.

10. A composition according to claim 4, wherein said at least one polysiloxane macromer (C) corresponds to the following formula:

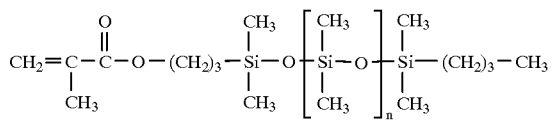

wherein n is a number ranging from 5 to 700.

11. A composition according to claim 1, wherein said at least one grafted silicone polymer is a copolymer obtained by radical polymerization from the mixture of monomers:

a) 60 weight % of tert-butyl acrylate;

b) 20 weight % of acrylic acid; and c) 20 weight % of silicone macromer of formula:

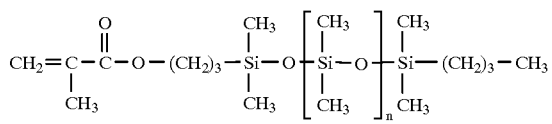

wherein n is a number ranging from 5 to 700, the percentages by weight being calculated with respect to the total weight of the monomers.

12. A composition according to claim 1, wherein said at least one grafted silicone polymer is a copolymer obtained by radical polymerization from the mixture of monomers:

a) 80 weight % of tert-butyl acrylate; and b) 20 weight % of silicone macromer of formula:

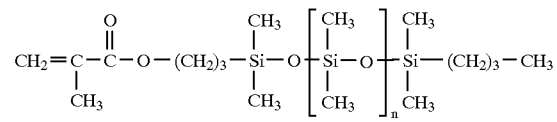

wherein n is a number ranging from 5 to 700, the percentages by weight being calculated with respect to the total weight of the monomers.

13. A composition according to claim 1, wherein said at least one grafted silicone polymer has a number-average molecular weight ranging from 10,000 to 2,000,000 and a glass transition temperature Tg or a crystalline melting temperature Tm of at least −20° C.

14. A composition according to claim 1, wherein said at least one grafted silicone polymer is a copolymer obtained by reactive extrusion of a polysilixone monomer, said polysiloxane monomer being a polysiloxane macromer having an end reactive functional group, with a non-silicone organic skeleton, said non-silicone organic skeleton being a polyolefin containing reactive groups capable of reacting with the end reactive functional group of the polysiloxane macromer to form a covalent bond enabling said polysiloxane macromer to be grafted to the polyolefin.

15. A composition according to claim 14, wherein said polyolefin is selected from polyethylenes and polymers of monomers derived from ethylene containing reactive functional groups capable of reacting with the end functional group of the polysiloxane macromer.

16. A composition according to claim 14, wherein said polyolefin is selected from copolymers of ethylene or of ethylene derivatives and at least one monomer selected from monomers containing a carboxyl functional group, monomers containing an acid anhydride functional group, monomers containing an acid chloride functional group, monomers containing an ester functional group, and monomers containing an isocyanate functional group.

17. A composition according to claim 14, wherein said polysiloxane macromer contains a functionalized group at or close to the end of the polysiloxane chain, wherein said functionalized group is selected from alcohols, thiols, epoxy groups and primary and secondary amines.

18. A composition according to claim 14, wherein said polysiloxane macromer corresponds to the general formula (III):

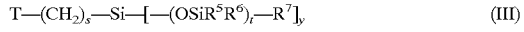 (III)

wherein T is selected from NH$_2$, NHR', an epoxy functional group, OH and SH; and wherein $R^5$, $R^6$, $R^7$ and R' independently denote a $C_{1-C6}$ alkyl, phenyl, benzyl, $C_{6-C12}$ alkylphenyl or hydrogen; s is a number from 2 to 100; t is a number from 0 to 1000 and y is a number from 1 to 3.

19. A composition according to claim 1, wherein said at least one grafted silicone polymer is present in an amount ranging from 0.01 to 20 weight % with respect to the total weight of the composition.

20. A composition according to claim 19, wherein said at least one grafted silicone polymer is present in an amount ranging from 0.1 to 15 weight %.

21. A composition according to claim 20, wherein said at least one grafted silicone polymer is present in an amount ranging from 0.5 to 10 weight %.

22. A composition according to claim 1, wherein said at least one ionic amphiphilic polymer is selected from:

(1) ionic holosides modified by groups containing at least one fatty chain;

(2) copolymers of maleic anhydride and of at least one monomer containing at least one fatty chain;

(3) copolymers of crotonic acid and of at least one monomer containing at least one fatty chain;

(4) copolymers of (meth)acrylic acid and of at least one monomer containing at least one fatty chain, wherein said at least one monomer containing at least one fatty chain is selected from hydrophobic monomers with a fatty chain and amphiphilic monomers containing a hydrophobic part with a fatty chain and a hydrophilic part.

23. A composition according to claim 1, wherein said at least one amphiphilic ionic polymer is present in an amount ranging from 0.01 to 20 weight % of the total weight of the composition.

24. A composition according to claim 23, wherein said at least one ionic amphiphilic polymer is present in an amount ranging from 0.1 to 15 weight %.

25. A composition according to claim 24, wherein said at least one ionic amphiphilic polymer is present in an amount ranging from 0.5 to 10 weight %.

26. A composition according to claim 1, wherein said composition further comprises at least one additive selected from thickeners without a fatty chain, fatty acid esters, esters of fatty acids and of glycerol, silicones, surfactants, fragrances, preservatives, sunscreening agents, proteins, vitamins, polymers, vegetable, animal, mineral or synthetic oils and any other additive conventionally used in the cosmetics field.

27. A composition according to claim 1, wherein said cosmetically or dermatologically acceptable medium comprises water or a mixture of water and at least one cosmetically acceptable solvent.

28. A composition according to claim 27, wherein said at least one cosmetically acceptable solvent is selected from monoalcohols, polyalcohols, glycol ethers, and fatty acid esters.

29. A composition according to claim 1, wherein said keratinous substance is human hair.

30. A composition according to claim 1, wherein said at least one grafted silicone polymer is dissolved in the cosmetically or dermatologically acceptable medium or is present in the form of an aqueous dispersion of particles.

31. A composition according to claim 1, wherein said composition is provided in the gel, milk, cream, more or less thickened lotion or foam form.

32. A composition according to claim 1, wherein said composition is a styling product.

33. A composition according to claim 1, wherein said composition is a hair product which is or is not to be rinsed out.

34. A composition according to claim 1, wherein said composition is packaged in the form of a vaporizer, in the form of a pump-action spray, or in an aerosol container for the purpose of obtaining a spray, a lacquer or a foam.

35. A process for the treatment of at least one keratinous substance, comprising applying to said substance a composition according to claim 1.

36. A process according to claim 35, further comprising the step of rinsing with water.

37. A process according to claim 35, wherein said at least one keratinous substance is human hair.

38. A composition according to claim 1, wherein said at least one grafted silicone polymer is a copolymer comprising:

a) 60 weight % of residues of tert-butyl acrylate;

b) 20 weight % of residues of acrylic acid; and c) 20 weight % of residues of silicone macromer of formula:

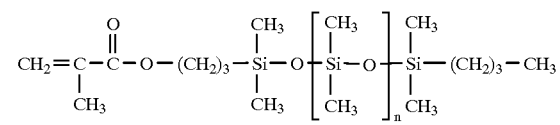

wherein n is a number ranging from 5 to 700, the percentages by weight being calculated with respect to the total weight of the residues of the monomers.

39. A composition according to claim 1, wherein said at least one grafted silicone polymer is a copolymer comprising:

a) 80 weight % of residues of tert-butyl acrylate; and b) 20 weight % of residues of silicone macromer of formula:

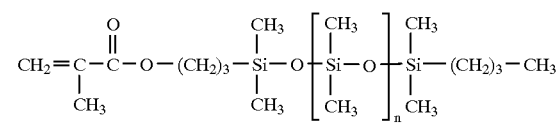

wherein n is a number ranging from 5 to 700, the percentages by weight being calculated with respect to the total weight of the residues of the monomers.

40. A composition according to claim 33, wherein said hair product is a shampoo.

41. A composition according to claim 1, wherein said composition is a hair product which is to be applied before or after shampooing, dyeing, bleaching, permanent waving or hair straightening.

* * * * *

UNITED STATES PATENT AND TRADEMARK OFFICE
CERTIFICATE OF CORRECTION

PATENT NO.:      6,090,376
DATED:           July 18, 2000
INVENTOR(S):     Claude DUBIEF et al.

It is certified that an error appears in the above-identified patent and that said Letters Patent is hereby corrected as shown below:

Claim 4, col. 10, line 34, change "$C_{6-C_2}$" to --$C_6$-$C_{12}$--.

Claim 5, col. 10, line 46, change "$C_{1-C18}$" to --$C_1$-$C_{18}$--.

Claim 9, col. 6, line 27, change "$C_{6-C12}$" to --$C_6$-$C_{12}$--;

col. 11, line 29, change "$C_{6-C12}$" to --$C_6$-$C_{12}$--.

Claim 14, col. 12, line 19, change "pol-" to --poly--;

col. 12, line 20, change "ysiloxane" to --siloxane--.

Claim 18, col. 12, line 53, change "$C_{1-C6}$" to --$C_1$ -$C_6$-- and change "$C_{6-C12}$" to --$C_6$-$C_{12}$--.

Signed and Sealed this

Seventeenth Day of April, 2001

Attest:

NICHOLAS P. GODICI

Attesting Officer      *Acting Director of the United States Patent and Trademark Office*